United States Patent
Kimura

[11] Patent Number: 5,940,126
[45] Date of Patent: *Aug. 17, 1999

[54] MULTIPLE IMAGE VIDEO CAMERA APPARATUS

[75] Inventor: Masanobu Kimura, Kamakura, Japan

[73] Assignee: Kabushiki Kaisha Toshiba, Kawasaki, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/547,554

[22] Filed: Oct. 24, 1995

[30] Foreign Application Priority Data

Oct. 25, 1994 [JP] Japan .................................. 6-260546

[51] Int. Cl.⁶ .................................................. H04N 5/225
[52] U.S. Cl. .......................... 348/294; 348/218; 348/65
[58] Field of Search ..................... 348/207, 335, 348/340, 343, 344, 373, 374, 65, 66, 218, 294; 600/101, 109; 359/434, 435, 618, 633, 656, 831, 834; H04N 5/225

[56] References Cited

U.S. PATENT DOCUMENTS

| | | |
|---|---|---|
| 2,854,901 | 10/1958 | Fathauer .................................. 348/343 |
| 4,167,756 | 9/1979 | Smith . | |
| 4,571,628 | 2/1986 | Thristol .................................. 348/211 |
| 4,622,954 | 11/1986 | Arakawa et al. ......................... 348/65 |
| 5,159,455 | 10/1992 | Cox et al. .............................. 348/312 |
| 5,386,228 | 1/1995 | Okino .................................... 348/218 |
| 5,547,455 | 8/1996 | McKenna et al. ....................... 348/65 |

FOREIGN PATENT DOCUMENTS

| | | |
|---|---|---|
| 1 442 335 | 5/1966 | France . |
| 38 06 190 | 9/1988 | Germany . |
| 1-121725 | 5/1989 | Japan . |
| 2 240 444 | 7/1991 | United Kingdom . |
| 93/11631 | 6/1993 | WIPO . |
| 93/21736 | 10/1993 | WIPO . |

Primary Examiner—Wendy Garber
Assistant Examiner—Tuan V. Ho
Attorney, Agent, or Firm—Pillsbury Madison & Sutro

[57] ABSTRACT

The present invention intends to provide a small video camera apparatus capable of imaging an object from various angles, and effectively monitoring an object or obtaining three-dimensional image information. A light beam supplied from an optical image passing through a lens is picked up by a right image sensing surface of a charge-coupled device, and a light beam supplied from an optical image passing through a lens and a prism is picked up by a left image sensing surface of the charge-coupled device. The image signals obtained by the right and left image sensing surfaces are divided in a color separating and signal processing circuit.

2 Claims, 5 Drawing Sheets

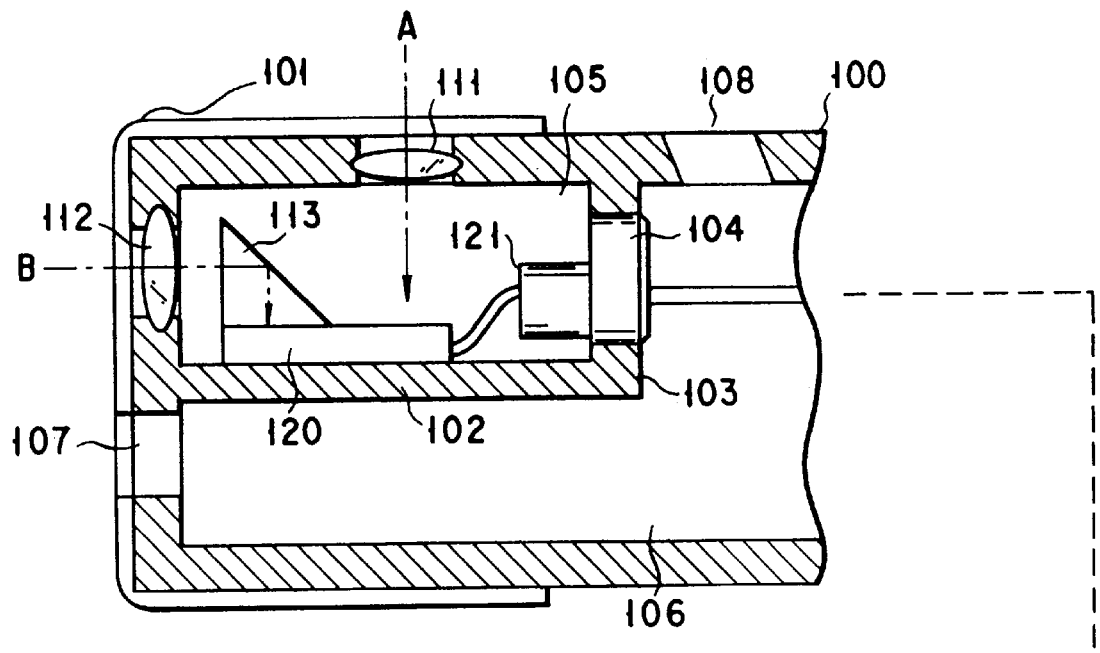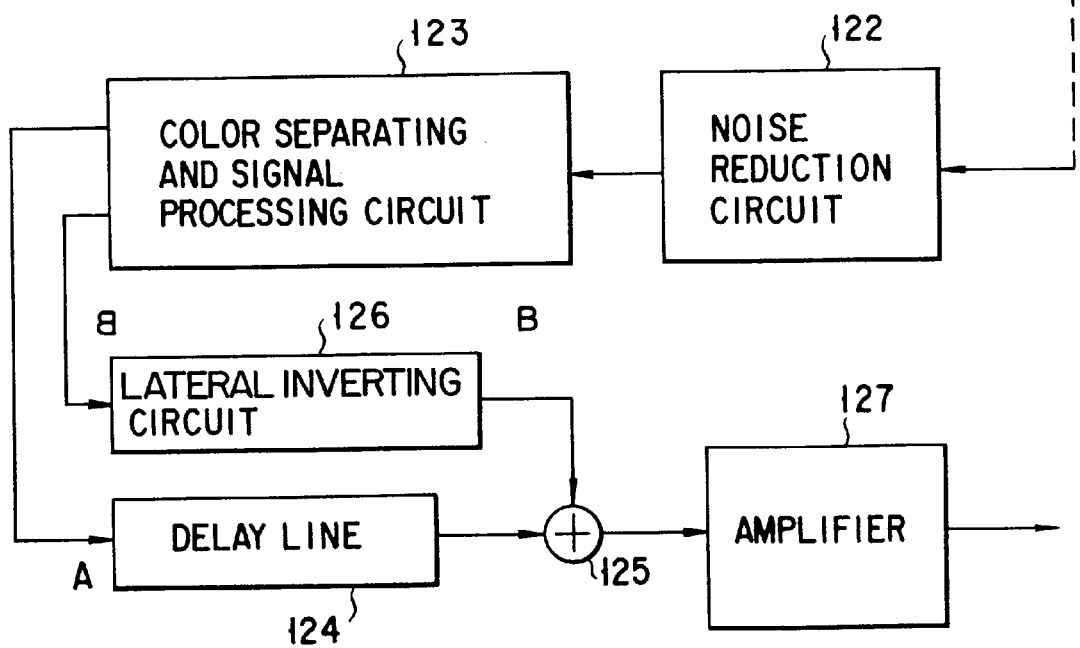
F I G. 1

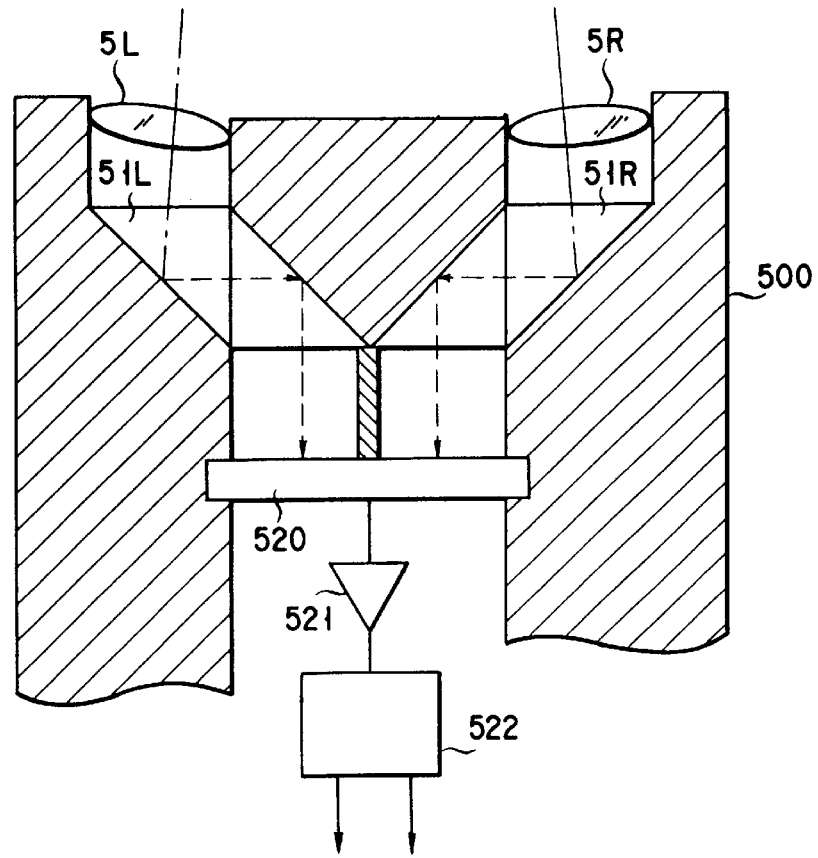
F I G. 5
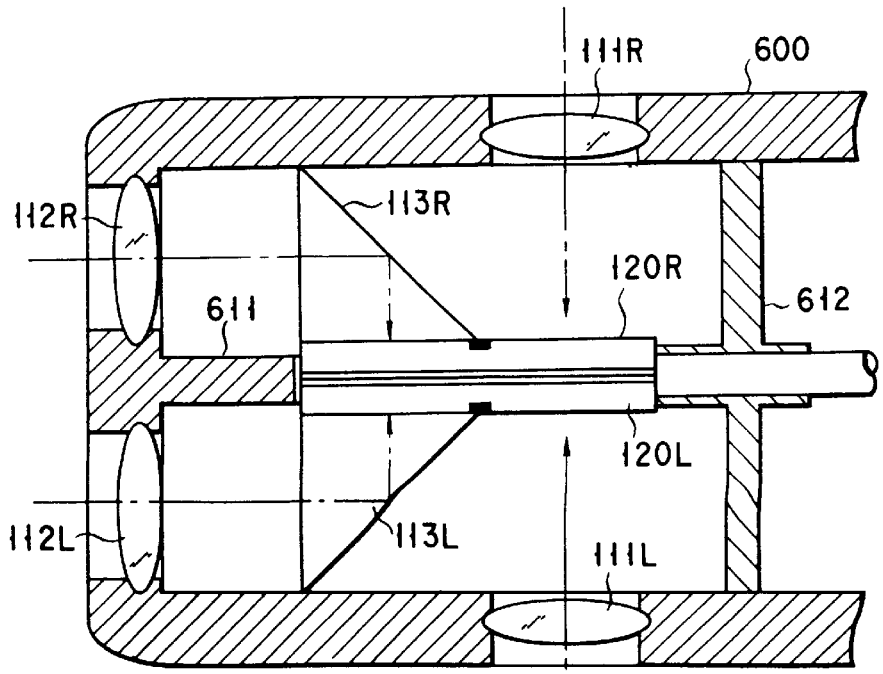
F I G. 6

MULTIPLE IMAGE VIDEO CAMERA APPARATUS

BACKGROUND OF THE INVENTION

1. Field of the Invention

This invention relates to a video camera apparatus useful as a monitoring camera, three dimensional camera, endoscopic camera, and so on.

2. Description of the Related Art

A system comprising a plurality of video cameras is known which is used as a factory monitoring camera system. In this system, the outputs from a plurality of cameras are input to an image synthesizer. The image synthesizer then outputs a synthesized image to be displayed on a monitor. This system using electronic endoscope cameras can provide both a front-view type camera and a side-view type camera depending on photographing conditions or requirements.

In the conventional monitoring system, a plurality of images photographed by multiple cameras are simultaneously displayed on one monitor by executing the image synthesizing, or different types of cameras are used separately in accordance with the photographing conditions. Therefore, the conventional monitoring system requires a plurality of cameras to simultaneously obtain a plurality of images. Similarly, when images in a plurality of directions are simultaneously required, the conventional electronic endoscope camera cannot provide the desired images.

SUMMARY OF THE INVENTION

The object of the present invention is to provide a small video camera apparatus capable of imaging an object from various angles.

Another object of the present invention is to provide a video camera apparatus useful as a monitor for obtaining image information or an apparatus for obtaining three-dimensional image information.

In order to attain these objects, a video camera apparatus according to the invention comprises: a body; first and second optical systems arranged at different positions on the body; a charge-coupled device provided in the body and having image sensing surfaces separated by a black portion, for generating an image signal from light beams supplied from the first and second optical systems, respectively; and dividing means for dividing the image signal representing a first image and a second image signal corresponding to the image sensing surfaces.

The video camera apparatus can generate image information from a plurality of angles by use of the small charge-coupled device formed in the body.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 shows a schematic drawing illustrating one embodiment of the video camera apparatus of the present invention;

FIG. 5 shows a schematic drawing illustrating still another embodiment of the video camera apparatus of the present invention;

FIG. 6 shows a schematic drawing illustrating further another embodiment of the video camera apparatus of the present invention.

DETAILED DESCRIPTION OF THE PREFERRED EMBODIMENTS

The embodiments of the present invention will be described below with reference to the drawings.

Figure 2A:
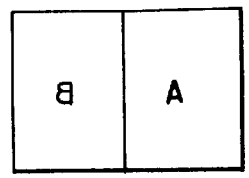
FIGS. 2A and 2B show schematic drawings illustrating the operation of the video camera apparatus shown in FIG. 1.
Figure 2B:
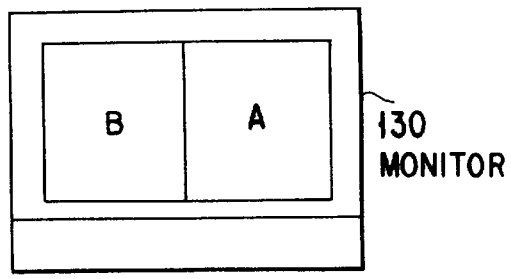
Figure 2C:
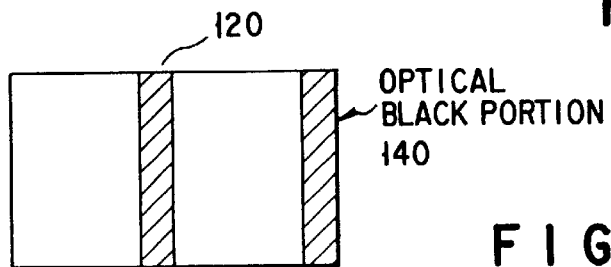
FIG. 2C shows a schematic drawing of the charge-coupled device formed in the video camera apparatus of FIG. 1.

FIG. 1 illustrates one embodiment of the present invention, FIGS. 2A and 2B show, in order to clarify the operation of the apparatus, arrangements of the images formed by use of the apparatus, and FIG. 2C illustrates the structure of the charge-coupled device as a solid state imager.

In FIG. 1, 100 denotes a body as a housing of the camera, for example, formed as a cylindrical shape. One end portion of the body is covered with a protector 101 made of a transparent material. In the body 100, a partition plate 102 is arranged in an axial direction. One end portion of the partition plate 102 is integrated with a rear plate 103 formed to be integrated with an inner wall on one side of the body 100. In the rear plate 103, a round hole is formed such that a bung 104 is attached therewith. The partition plate 102, rear plate 103, and a part of the inner wall of the body 100 form a container section 105. The container section 105 is concealed to prevent the permeation of water.

The side wall of the body 100 forming the container 105 is provided with a lens 111 so as to obtain images on the side of the body. The front wall of the body 100 which also forms the container 105 is provided with a lens 112 so as to obtain images in front of the body. The light beam supplied from an optical image A passing through the lens 111, for example, is picked up by an image sensing surface of the charge-coupled device 120, which is arranged on the right side, for example. Similarly, the light beam supplied from an optical image B through the lens 112 passes through a prism 113 and turns its passing direction and is picked up by an image sensing surface of the charge-coupled device 120, which is arranged on the left side, for example.

FIG. 2A schematically illustrates images A and B read as photoelectrically converted images after the images are picked up by the image sensing surfaces of the charge-coupled device 120. The image B is laterally inverted (left to right) when the direction in which the light beam passes is turned due to the prism 103.

The photoelectrically converted signal of the charge-coupled device is output to an amplifier 121 and undergoes a noise reduction process in a noise reduction circuit 122. The signal output from the noise reduction process is input to a color separating and signal processing circuit 123 so as to be decoded as a standard video signal. The signal processing circuit 123 divides the images A and B by outputting each of the image signals A and B separated from each other. The dividing process is executed by a method in which, the output signals are divided in the midst of a horizontal scanning, for example, by use of a switch. If the images A and B are parallelly located in a vertical direction, the signals are divided in the midst of a vertical scanning by use of the switch.

The image signal of the image A is supplied to a synthesizer 125 through a delay line 124. While, the image signal of the image B is input to an image inverting circuit 126 to be laterally inverted and then supplied to the synthesizer 125. The synthesizer 125 synthesizes the image signal of the image B output from the image inverting circuit 126 and the image signal of the image A output from the color separating and signal processing circuit 123, and converts the time-multiplied signal into a video signal to be displayed as one synthesized image. The output of the synthesizer 125 is supplied to a monitor 130 through the amplifier 127. In this manner, the images A and B are displayed on the monitor 130 so as not to be inverted, as shown in FIG. 2B. The inverting process of the image inverting circuit 126 is executed for inverting the time axis of the horizontal scanning of the image signals by using a memory device. Due to this process of the image circuit 126, the time delay occurs in the signal propagation of the image B. In order to make the image signal for the image A arrive at the same time as the image signal of the image B, the image signal of the image A is delayed by the delay line 124 before the signal is input to the synthesizer 125.

In a conventional charge-coupled device, an optical black portion 140 shown in FIG. 2C is arranged on one end portion of the horizontal scanning in order to prevent the influence of a dark current. In addition to the optical black portion, the charge-coupled device 120 of the present invention is supplied with an image separating black portion 141 for shielding light in the midst of the device. The image separating black portion 141 is formed by use of a photolithography or painting method to apply an aluminum layer on a transparent protective film as an insulating layer formed on a sensing section of the charge-coupled device.

If the video camera of this embodiment is intended to obtain both the image A in front of the body and the image B located above or below the body, the abovementioned lateral image inverting process is replaced with a vertical image inverting process.

In addition, the effect of the image separating black portion 141 on the charge-coupled device 120 is shown as a black belt-like zone in the central portion of the display when the output of the charge-coupled device 120 is displayed without any processing. This zone can be removed from the displayed image by changing the period of time set for reading a signal from the lateral inverting circuit 126 or adjusting the delay time of the delay line 124.

Figure 3A:
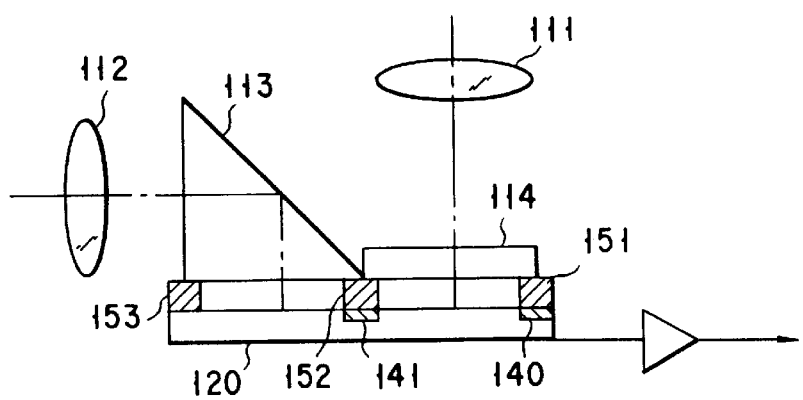
FIG. 3A shows a schematic drawing illustrating a charge-coupled device section of the video camera apparatus of the present invention.

FIG. 3A presents a sectional view illustrating a specific embodiment of the charged-coupled device 120. On the charge-coupled device, integrated shielding members 151, 152, and 153 are arranged immediately on the optical black portion 140, the image separating black portion 141, and a starting point of the horizontal line, respectively. In particular, the shielding member 152 is provided to shield the light beams passing through the space between left and right image areas in order to prevent the interference between the light beams supplied from the image areas. The shielding members 151, 152, and 153 are also used as a spacer for connecting the prism 113, a protective glass layer 114, and the charge-coupled device 120 to each other.

Figure 3B:
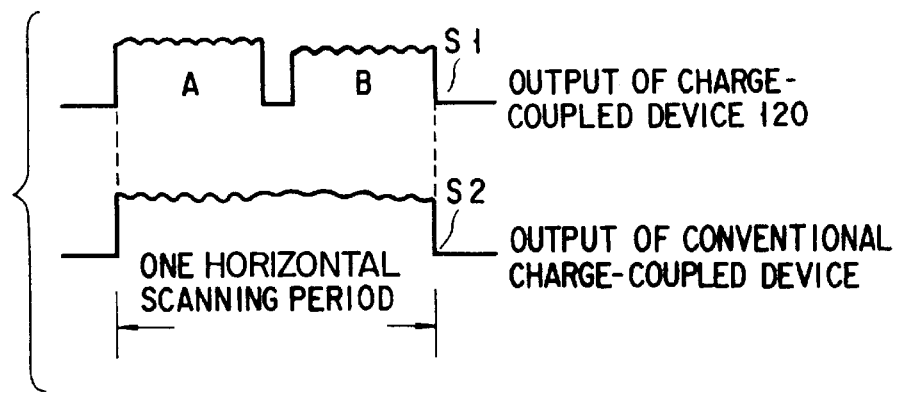
FIG. 3B shows a timing chart of the signals read from the charge-coupled device.

FIG. 3B shows a timing chart for comparing a signal S1 generated by the charge-coupled device 120 of the present invention and a signal S2 generated by the conventional charge-coupled device. The timing chart clearly shows that, according to the charge-coupled device 120 of the present invention, image signals of two images can be obtained even in accordance with the conventional image reading process.

The above-mentioned embodiment relates to an example for imaging objects located in two directions. The present invention, however, is not limited to the above embodiment.

FIG. 1 will be described again.

In the body 100 of FIG. 1, there is a space on the opposite side of the container section 105 with regard to the partition plate 102, i.e., under the container section 105. In the front of the space 106, a through hole 107 is provided. This hole can be used as a hole in which a lighting device for lighting the front of the body, or a forceps used for a surgical operation or the like is fitted. In FIG. 1, only one through hole 107 is illustrated, but a plurality of holes are provided to the apparatus, in fact. Similarly, the side wall of the body 100 is also provided with a through hole 108 for providing a lighting.

The video camera apparatus shown in FIG. 1 effectively works as a medical camera. For example, when a stomach is monitored by use of this camera, the images of the portions located in front and on the side of the camera can be simultaneously obtained without turning the camera.

In the signal processing of the video camera of the present invention, the color separating and signal processing circuit 123 executes a color signal generating process, then executes a separation of the images. In the signal processing, the color signal generating process is executed at first so as not to prevent the color synchronization. If the separation of the images were executed at first, the original color of the images could not be precisely reproduced.

In FIG. 1, the body is defined as a cylindrical shape. However, the body may be formed as an oval, or triangle or square pole. The charge-coupled device 120 is described as a color charge-coupled device having color filters, but may be a monochrome charge-coupled device, of course. The body may be also formed with a transparent material so as to be integrated with the lenses.

Further, when the body 100 contains the noise reduction circuit 122, color separating and signal processing circuit 123, image inverting circuit 126, delay line 124, synthesizer 125, and amplifier 127, the body 100 forms a sufficiently waterproofed and vibration resistant structure. In this embodiment, the elements are contained within the body 100, but may be formed out of the body 100 at a distance. Similarly, the outputs from the image inverting circuit 126 and the delay line 124 are synthesized by the synthesizer 125, but may be input to different monitors respectively.

Figure 4A:
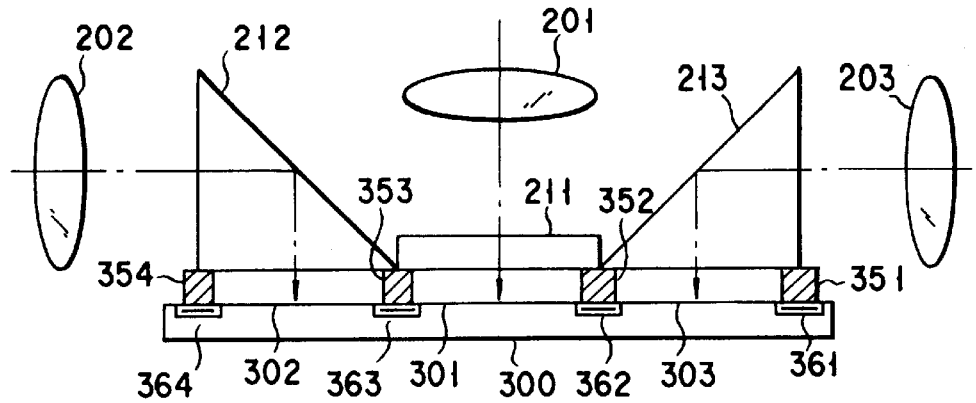
FIG. 4A shows a schematic drawing illustrating another embodiment of the video camera apparatus.

FIG. 4A shows another embodiment of the present invention.

As shown in FIG. 4A, the apparatus of this embodiment is provided with first, second, and third lenses 201, 202, and 203. The first lens 201 gets a ray from the object and an image passes through a protective glass layer 211 and is picked up by an image sensing surface 301 located in the middle of a charge-coupled device 300. Similarly, the second lens 202 gets a light beam supplied from the object located on the left side and the light beam supplied from the image passes through a prism 212 and is picked up by an image sensing surface 302 located on the left side of a charge-coupled device 300. The third lens 203 also gets a light beam from the object and an image passes through a prism 213 and is picked up by an image sensing surface 303 located on the right side of a charge-coupled device 300. In FIG. 4A, reference numbers 351, 352, 353, and 354 denote shielding members for optically separating the image sensing surfaces from each other. Immediately under the shielding members 351, 352, 353, and 354, image separation black portions 361, 362, 363 and 364 are formed in the charge-coupled device 300.

Figure 4B:
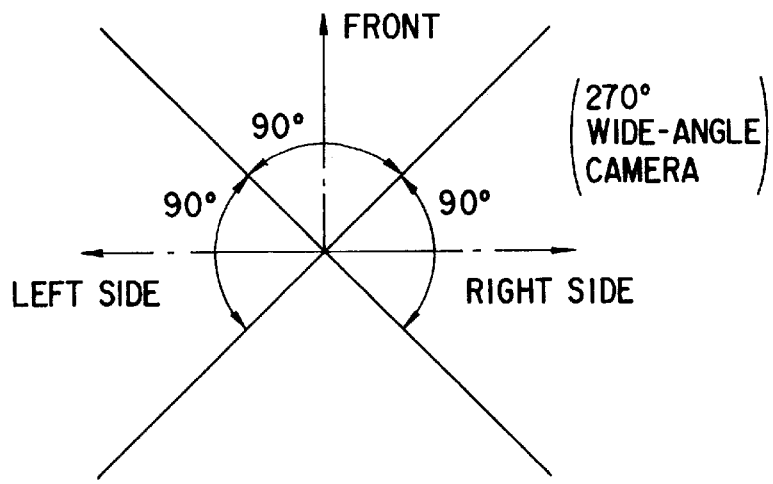
FIG. 4B shows a drawing showing an imaging area of the video camera apparatus.
Figure 4C:
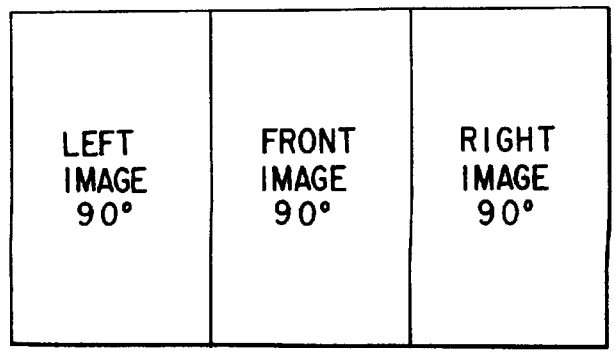
FIG. 4C shows a drawing illustrating an image formed by the video camera apparatus.

By virtue of this structure, the video camera apparatus can be formed as a wide-angle camera which has an imaging area of 270° as shown in FIG. 4B and will not cause large optical distortion. According to this camera, front, left, and right images can be displayed on the monitor as shown in FIG. 4C.

This video camera apparatus effectively works as a monitoring camera. If this camera is equipped in a car, the driver can easily monitor the front, left, and right directions. The camera can be set up in the rear of a car to effectively monitor the back, left and right.

The present invention is not limited to the above-mentioned embodiments, but can be used as a three-dimensional video camera.

FIG. 5 presents an example of a three-dimensional video camera.

A body 500 is provided with left and right imaging lenses 5L and 5R each having a convergence angle. The light beam supplied from optical images AL and AR pass through the lenses 5L and 5R and arrive at the left and right portions of the image sensing surface of the charge-coupled device 520 through prisms (or reflecting mirrors) 51L and 51R. Image signals generated by the charge-coupled device 520 are input into an image dividing circuit 522 through an amplifier 521 and divided into left and right image signals. The user can obtain a three-dimensional image on the basis of the left and right images by a method using a peephole or glasses.

FIG. 6 shows still another embodiment of the present invention.

In this embodiment, charge-coupled devices 120R and 120L are coupled back to back with an adhesive and arranged to hold a central axis of a body 600 therebetween. Lenses 111R and 111L are arranged oppositely to the rear portions of image sensing areas of the charge-coupled devices 120R and 120L. The lenses 111R and 111L are fixed to the side walls of the body 600. The front portions of the image sensing areas of the charge-coupled devices 120R and 120L are provided with prisms 113R and 113L respectively so as to be integratedly formed therewith. The prisms 113R and 113L respectively receive the optical images passing through lenses 112R and 112L. The lenses 112R and 112L is set in and fixed in holes in a front wall of the body 600.

The front edges and the side edges of the charge-coupled devices 120R and 120L are supported by a supporting member 611 formed in the body 600, and the rear edges of the charge-coupled devices 120R and 120L are supported by a fixing member 612. The fixing member 612 has guiding portions for guiding wirings connected to the charge-coupled devices 120R and 120L.

According to the video camera apparatus of this embodiment, the images of the front and left and right sides of the object can be obtained, and thus the imaging area can be enhanced. How to process and display the imaging signals is determined by a video signal processing circuit for dividing the imaging signals.

In the above embodiment, the supporting member 611 is arranged in the body 600. The supporting member 611, however, can be also formed as the rotation axis of a body 600 arranged in the center of the body 600. In this case, the charge-coupled devices 120R and 120L and prisms 113R and 113L are integrated and rotatably arranged in the body. The integrated element is called an imaging unit. In this structure, lenses having a magnification different from the lenses 111R and 111L may be provided on the circumference of a circle of the section of the body, on which the lenses 111R and 111L are arranged. By providing the lenses with different magnifications in this manner, the user can select a most suitable lens to obtain an image of the object in accordance with the distance between the body and object.

As described above, according to the present invention, a small video camera apparatus capable of imaging an object from various angles, and effectively obtaining three-dimensional image information, can be obtained.

Figure 7:
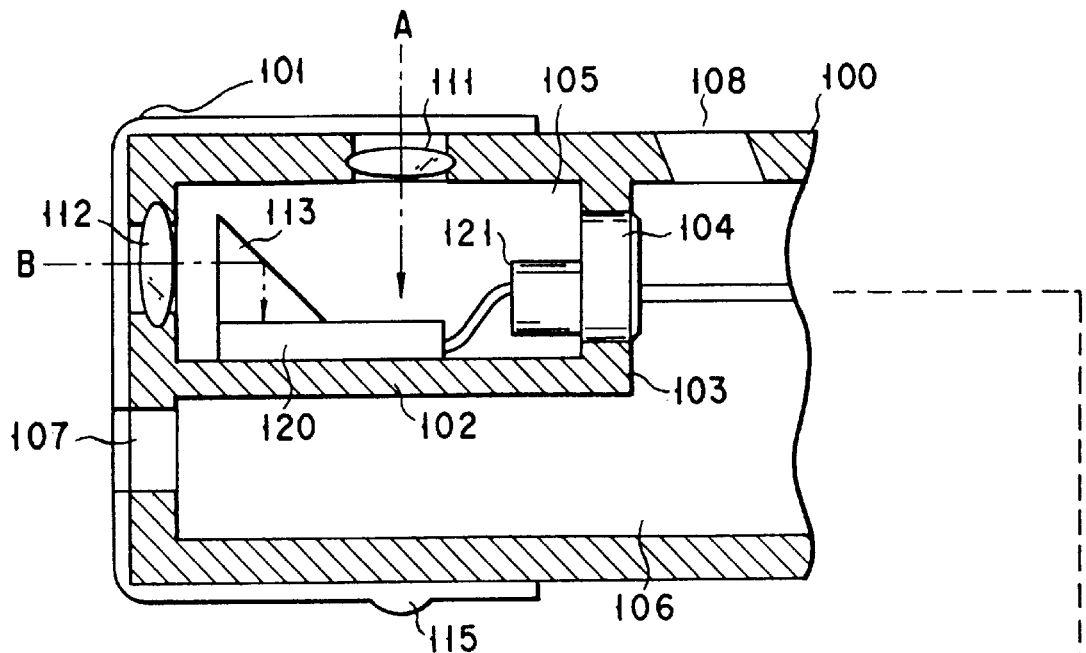
FIG. 7 shows a schematic drawing illustrating another embodiment of the video camera apparatus.
Figure 7:
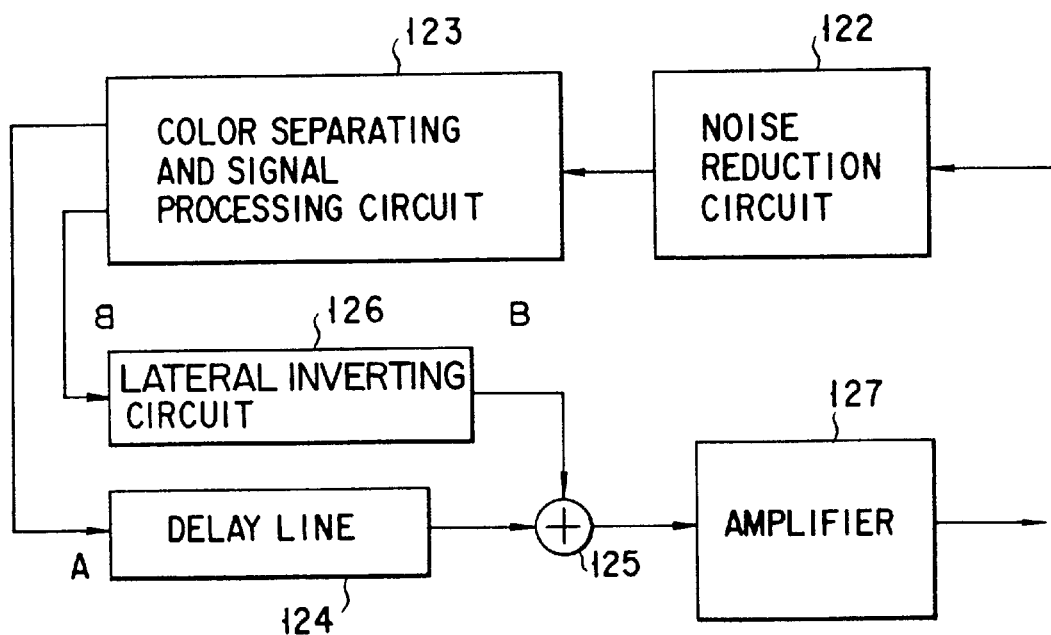

FIG. 7 shows another embodiment of the present invention.

In this embodiment, the protector 101 has a plurality of converting lenses 115, 116, 117, . . . (116, 117 are not shown) on the circumference, and the protector 101 can rotate on the body 100, then one of converting lenses is selected to correspond with the lens 111. According to this embodiment, different magnification images are obtained by switching the converting lenses. The remaining elements within FIG. 7 are the same as FIG. 1.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A video camera apparatus comprising:

a body;

first and second optical systems arranged at different positions on the body;

a charge-coupled device provided in the body and having image sensing surfaces separated by a black portion, for generating an image signal from light beams supplied from the first and second optical systems, respectively;

dividing means for dividing the image signal representing a first image and a second image signal corresponding to said image sensing surfaces;

a lateral image inverting circuit for inverting a time-axis of a horizontal scanning of one of the signals divided by the image signal dividing means; and converting means for time-multiplying a second image signal output from the lateral image inverting circuit and said one of the signals divided by the image signal dividing means so as to convert the image signals into one video signal.

2. A video camera apparatus comprising;

a body;

first and second optical systems arranged at different positions on the body;

an image sensing device provided in the body and having image sensing surfaces separated by a black portion, for generating an image signal from light beams supplied from the first and second optical systems, respectively;

dividing means for dividing the image signal representing a first image and a second image signal corresponding to said image sensing surfaces;

a lateral image inverting circuit for inverting a time-axis of a scanning direction of one of the signals divided by the image signals divided by the image signal dividing means; and converting means for time-multiplying a second image signal output from the lateral image inverting circuit and said one of the signals divided by the image signal dividing means so as to convert the image signals into one video signal.

* * * * *